(12) United States Patent
Basler

(10) Patent No.: US 7,178,731 B2
(45) Date of Patent: Feb. 20, 2007

(54) MEASURING DEVICE FOR A MODEL AND MACHINING DEVICE EQUIPPED WITH THE SAME

(75) Inventor: Franz Basler, Laudenbach (DE)

(73) Assignee: Sirona Dental Systems GmbH, Bensheim (DE)

(*) Notice: Subject to any disclaimer, the term of this patent is extended or adjusted under 35 U.S.C. 154(b) by 0 days.

(21) Appl. No.: 10/522,015

(22) PCT Filed: Jul. 22, 2003

(86) PCT No.: PCT/DE03/02457

§ 371 (c)(1),
(2), (4) Date: Jan. 21, 2005

(87) PCT Pub. No.: WO2004/016189

PCT Pub. Date: Feb. 26, 2004

(65) Prior Publication Data

US 2005/0254064 A1    Nov. 17, 2005

(30) Foreign Application Priority Data

Jul. 22, 2002    (DE) .............................. 102 33 314

(51) Int. Cl.
*G06K 7/10*    (2006.01)
(52) U.S. Cl. .................. 235/462.01; 235/454
(58) Field of Classification Search ........... 235/462.01, 235/462.13; 425/2; 264/16
See application file for complete search history.

(56) References Cited

U.S. PATENT DOCUMENTS

| 6,459,477 B1 * | 10/2002 | Berlin et al. .................. 356/73 |
| 6,614,538 B1 | 9/2003 | Basler et al. |
| 2002/0076530 A1 | 6/2002 | MacDougald et al. |
| 2003/0068079 A1 * | 4/2003 | Park .......................... 382/154 |
| 2003/0132539 A1 | 7/2003 | Althoff et al. |

FOREIGN PATENT DOCUMENTS

| CA | 2 322 761 | 9/1999 |
| CA | 2 392 325 | 6/2001 |
| DE | 40 30 176 | 3/1992 |
| WO | WO 99/13796 | 3/1999 |

* cited by examiner

Primary Examiner—Michael G. Lee
Assistant Examiner—Kristy A. Haupt
(74) Attorney, Agent, or Firm—Dykema Gossett PLLC

(57) ABSTRACT

The invention relates to a measuring device comprising elements for measuring models for producing dental fittings by generating a three-dimensional data record as a model for the three-dimensional machining of a workpiece. The measuring elements are configured in such a way that they can also detect an identification comprising information about the workpiece. The invention also relates to a machining device for producing dental fittings from a workpiece. The device comprises a receiving device for the workpiece, an identification comprising information about the workpiece being applied to the workpiece or workpiece holder. In addition, elements for detecting the identification of the workpiece that is held in the receiving device are provided and a single measuring device is used to measure the model and to detect the identification.

17 Claims, 2 Drawing Sheets

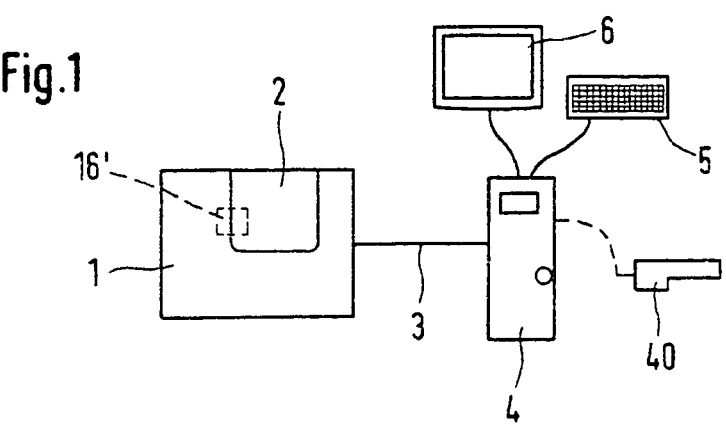
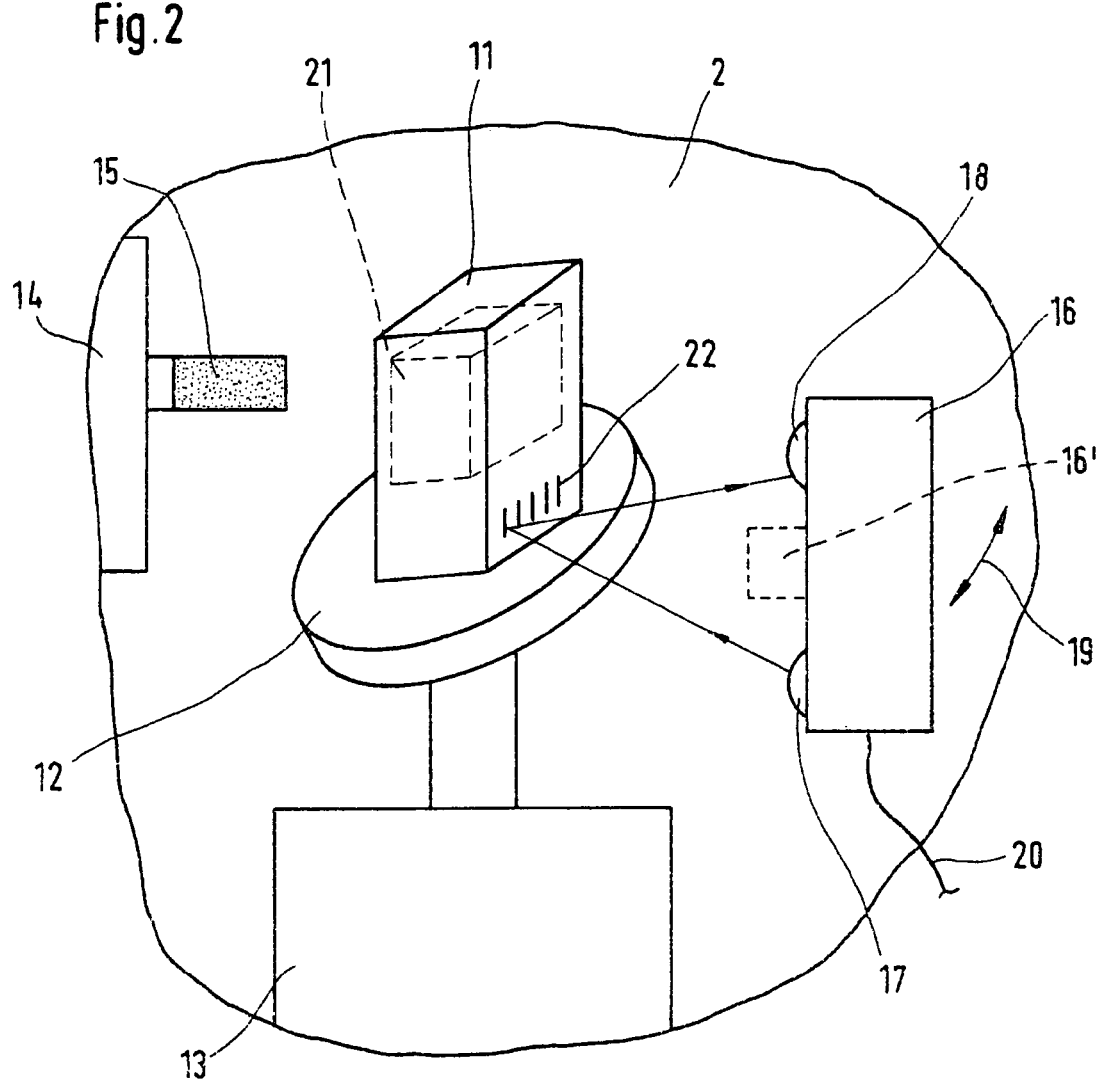

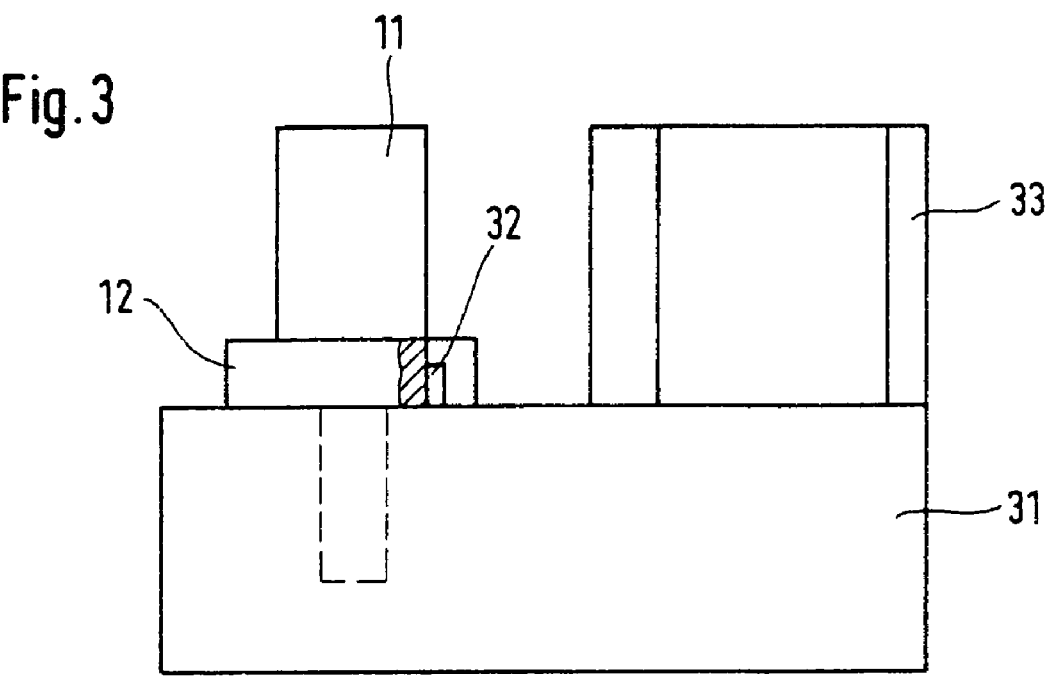
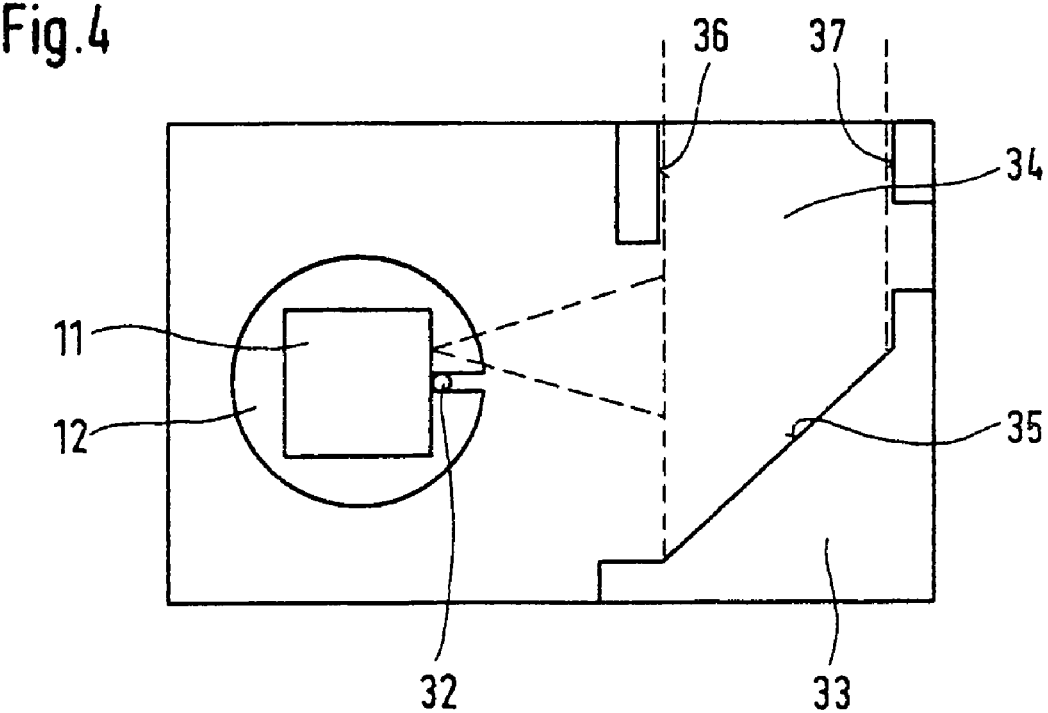

MEASURING DEVICE FOR A MODEL AND MACHINING DEVICE EQUIPPED WITH THE SAME

FIELD OF THE INVENTION

The invention relates to a measuring device, in particularly a measuring device forming part of a machining device, suitable for measuring a model for the purpose of fabricating a shaped object from, in particular, a dental ceramic. The invention also relates to machining equipment provided with such a measuring device.

When blanks in the form of partially cured ceramic blocks are machined and are subjected to a sintering process following machining to achieve final strength values, they must be fabricated larger than the finished product for the reason that they shrink during the sintering process. The shrinkage parameters of, for example, dental ceramics are usually dependent on the batch from which the blanks have been formed. Thus these shrinkage parameters will have to be known prior to machining for inclusion in the computation of the semifinished product to be fabricated by such removal of material.

DESCRIPTION OF RELATED ART

According to U.S. 2003/0132539 the shrinkage parameters are displayed on the holder in the form of a printed bar code. U.S. 2002/0076530 discloses an identifier only generally. It is also known to place the identifier on the ceramic block itself.

DE 40 30 176 A1 discloses a grinding machine that has a keyboard, a video monitor and a scanning camera. Furthermore, U.S. Pat. No. 6,614,538 discloses a system comprising a measuring device and machining equipment for the production of a fitting for tooth restorations.

From the prior art it is known to connect up a commercial bar-code scanner, which will read the enciphered shrinkage data in a bar code located on the blank. This is basically described in CA 02392325. Furthermore, it is known to collect the data by actuating the keyboard of the PC.

The first solution requires a separate bar-code reader, usually in the form of a scanner, while the second solution involving manual input is frequently prone to errors.

Furthermore, the company Degussa/Dentsply markets a set of equipment under the Trade Name Gereon which combines machining of a workpiece, 3D measuring of a model, and bar code reading of an identifier located on the workpiece in a single set but at different locations therein and using different means for each operation. Here again, there is still a source of error due to the fact that following recognition of the identifier on the blank to be machined the blank might be replaced by another if, say, it should be laid aside before it has been mounted in the workpiece holder.

It is an object of the invention to develop a measuring device such that the information specific to the particular material, in particular the shrinkage parameters, can be collected without high expenditure and with a high degree of error protection.

Furthermore, the invention relates to a machining device with which the risk of confusing the marked workpieces is further reduced.

SUMMARY OF THE INVENTION

This object is achieved as defined in claim 1. Advantageous embodiments are defined in the sub-claims.

In the measuring device having means for measuring models for the fabrication of dental fittings by creating a three-dimensional data set as template for three-dimensional machining of a workpiece, the said measuring means are also adapted for recognition of an identifier containing information on the workpiece.

By this means it is possible, using a measuring device that is necessary in any case, to carry out both the operation of measuring the model for the purpose of creating the data set necessary for fabrication of the shaped article and the operation of recognizing the identifier on the workpiece from which the shaped article is to be machined.

Optical recognition is particularly suitable when the identifier is in the form of a bar code, numerical code or color code. In addition, optical measuring is possible in the case of an identifier in the form of a shape code or relief code. Basically it is alternatively conceivable that recording of the model be carried out by electronic scanning, in which case the identifier would also be scanned electronically.

The means for recognizing an identifier can take the form of a sensor that registers an identifier in the form of differences in brightness located on the workpiece, or alternatively they can consist in image recognition of a measured intensity image which registers, for example, an identifier applied to the workpiece and taking the form of differences in brightness or of even an alphanumerical sequence. The sensor can also be adapted such that it can register an identifier located on the workpiece and configured in the form of differences in height.

Advantageously, said means for recognition of an identifier comprise an optical sensor for distance measurement. The output of the sensor can be governed by the intensity, while the variable controlling the output is dependent on the identifier.

According to a further embodiment, software for the production of the fitting is present, which software is designed such that the information gained from the identifier will be taken into consideration in computation of the fitting to be fabricated and/or for the control of the machining equipment and/or will be used for documentation purposes. The documentation comprises, in addition to storage of the information provided by the identifier, the provision of information for the purpose of further processing such as accounting, quality checking, etc.

Advantageously, the identifier is in the form of a bar code capable of being recognized by the measuring device. This makes it possible to use existing coding systems.

In a further development, the measuring device is part of a machining device for the fabrication of dental fittings from a workpiece. The machining device has a workholding device for the workpiece, which is also suitable for the accommodation of a model to be mapped or has another workholding device for this purpose. The measuring device will recognize the identifier of the workpiece held in the workholding device, on which workpiece an identifier containing information on the workpiece is located. The identifier may, if desired, be located on the workpiece holder, provided that said identifier will remain recognizable in the clamped position. In this case the workpiece will be identified in the workholding device in which it will be subsequently machined.

Advantageously, the measuring device used for measuring purposes and for recognizing the identifier is removably mounted on the machining device. This makes it possible for recording of the model and recognition of the identifier to be carried out in different places. For example, measuring can take place in the oral cavity of a patient and recognition of the identifier in the machining equipment.

Another object of the invention consists in a machining device for the production of dental fittings from a workpiece, which machining device has a workholding device for the workpiece. An identifier containing information on the workpiece is applied to the workpiece or to a workpiece holder. Furthermore, means are provided for recognizing the identifier of the workpiece held in the workholding device.

The advantage of this is that identification of the workpiece must take place just prior to machining without the workpiece having to be modified in any way. This effectively avoids any incorrect assignment of workpiece information.

The workholding device can also be adapted to accommodate a model to be measured so that a single measuring device of the invention can be used for measuring the model on the one hand and for recognizing the identifier on the other hand.

The machining device can be provided with a holder for releasable accommodation of the measuring device. By this means it is possible to carry out measuring at a different location, if desired.

Advantageously, software for fabrication of the fitting is present. The software is designed such that the information gained from the identifier will be taken into consideration for computation of the fitting to be fabricated and/or for the control of the machining equipment and/or will be used for documentation purposes. In particular, considerable advantages are gained from controlling the machining equipment while taking into consideration the information provided by the identifier in that, for example, the rate of advance can be regulated according to the material being machined or considerations of minimum wall thicknesses dependent on the stability of the material can influence the design.

BRIEF DESCRIPTION OF THE DRAWINGS

The drawings illustrate an embodiment of the invention, in which:

FIG. 1 is a diagram showing the setup of a machining device of the invention including a measuring device of the invention connected to a computer;

FIG. 2 is a detailed view of the machining chamber of the machining device.

FIG. 3 is a side view of a recognition unit for a measuring device,

FIG. 4 is a top view of the recognition unit shown in FIG. 3.

DETAILED DESCRIPTION OF PREFERRED EMBODIMENT

FIG. 1 illustrates a machining device 1 containing a machining chamber 2 connected by an interconnection cable 3 to a computer (PC) 4. The computer can, if desired, be incorporated in the casing of the machining equipment. PC 4 is provided with an input device in the form of a keyboard and an output device in the form of a video monitor 6. Interconnection cable 3 can transfer the data required for operation of the machining device.

In machining chamber 2 the following operations take place: machining of a workpiece and measuring of either an original object of which a copy is to be fabricated or a three-dimensional template to be supplemented by the fitting to be fabricated, or scanning to determine the position of the workpiece to be machined.

If no measuring is to be carried out in machining chamber 2, a scanning camera 40 can be provided, which is connected to the computer and with which, for example, recordings of the interior of the mouth of the patient are made.

In this case however, means 16' for recognition of the identification mark that are independent of measuring device 16 can be provided in machining chamber 2 so that even when no measuring is possible, recognition of the identification mark of the clamped blank 11 will be possible.

FIG. 2 illustrates a partial region of machining room 2 in greater detail. The Figure shows a workpiece in the form of a blank 11 of a well-known dental ceramics type and yet to be machined, this blank 11 being attached to a holder 12, and holder 12 being clamped in a workholding device 13.

In machining chamber 2 there is additionally provided at least one tool 14 having a grinding pin 15 adapted to remove material from the blank 11 when contacting same and being caused to execute rapid rotation.

Furthermore, there is provided in machining chamber 2 a measuring device 16, which in the present embodiment is in the form of a position-sensitive sensor. Measuring device 16 comprises a projection unit 17, which emits a measuring ray, and a receiving unit 18, on which a back-scattered reception ray impinges after reflection from the blank. Measuring device 16 can be shifted relatively to blank 11, as indicated by the arrow 19. Such a measuring device is illustrated and explained in U.S. Pat. No. 6,614,538 and the embodiments disclosed therein are incorporated herein by reference. In particular, measuring device 16 may be mounted on tool 14, if desired, and moved together with same.

The size and shape of the blank is such that the shaped object 21 to be fabricated can be cut out of blank 11. Furthermore, blank 11 has an identifier 22 containing information on, inter alia, the material of the blank. Identifier 22 is in the form of a bar code in which the width of the individual bars and the spaces between them denote a certain sequence of characters. The bars and interstices can, on account of their difference in brightness, be read by a bar-code scanner and converted by software to analyzable data. The bars are usually printed on the blank or on the holder.

Instead of implementing brightness information, an identifier may be provided which provides height-depth information and can be imparted to the blank by, say, a laser beam.

Signals recognized by measuring device 16 are transmitted through an interconnection cable 20 to the machining device and, optionally after the latter has executed initial machining, then sent through interconnection cable 3 (FIG. 1) to the computer. In this way, identifier 22 is evaluated by the software running in computer 4.

The sequence of events occurring when a machining device of the invention is used is as follows. Starting from a data set relevant to a shaped object to be fabricated and obtained by contactless measuring, electronic scanning or computer-aided design (CAD) and stored in computer 4 for use on demand, the user will select a blank 11 from which the said shaped object is to be cut out. Alternatively, the data set can be obtained by clamping a model into the workholding device for the workpiece followed by measuring thereof using measuring device 16.

Blank 11 can be of a material such as can still be thermally treated following machining. A particularly suitable material for this purpose is an incompletely sintered ceramic.

This material changes its shape in a foreseeable manner during heat treatment but the specific properties of the material depend on its manufacturing conditions and can vary from batch to batch. In the case of the aforementioned incompletely sintered dental ceramic a sintering process is carried out after the machining step, during which process the shaped article acquires greater stability. However, the heat treatment applied during sintering also causes shrinkage.

Thus, when designing the shaped object to be produced by machining, it will be necessary to take into consideration the change of dimensions that occur during shrinking. Thus the said shaped object must be produced overlarge so that the subsequent shrinkage will bring it to the desired size. Modification of the data set concerning the shaped object to be fabricated is effected by the software on the basis of the information specific to the particular material as provided by identifier 22, so that a corrected data set will be used for the production of the shaped object.

In addition to the shrinkage parameters, identifier 22 may provide other information on, say, the hardness of the material, the type of material used, the grain size, the size of the block, the shape of the block, its color, its serial number or other identifying features of the individual piece, and other information.

Based on this information, it will be possible to infer the machining rate, the tool to be used, the minimum wall thicknesses allowed and other important factors for the machining operation and to instruct the software to take such factors into account when generating the corrected data set.

Particularly suitable machining tools are grinding wheels, cylindrical grinders or conical grinders.

As mentioned above, the measuring device can serve to three-dimensionally measure a model of the part to be fabricated. However, it may also be used for the purpose of ascertaining the orientation of blank 11 in machining chamber 2 and with reference to its holder 12, possibly also in order to ascertain the position of tool 15. Measuring devices and measuring methods of this kind are well known in the prior art.

Due to the development achieved by the invention, these measuring devices can now be used for the recognition of an identifier.

In the case of the position-sensitive sensor 16 illustrated in FIG. 1, the power output of a laser diode is regulated according to the intensity of the light in the receiving photodiode (U.S. Pat. No. 6,614,538), so that the controlled variable for the power output allows for conclusions on identifier 22 in the form of a bar code. Alternatively, the intensity itself can be evaluated whilst the power of the laser diode is set at a fixed value.

A blank that is provided with an identifier will be spatially positioned relatively to the sensor in such a way that the sensor will read the identifier.

When a dark-colored area of the identifier is registered which only weakly reflects the incident light, low intensity is measured and the power output rises. Vice versa, when a light-colored area of the identifier is registered, increased intensity is measured and the necessary power output drops. On the basis of these changes, the material characteristics enciphered in the identifier in the form of a bar code will be recognized.

As mentioned above, the identifier can be located on the workpiece in the form of differences in height so that detection of the identifier will involve registering and evaluating not areas of different intensity but areas of different height.

Alternatively, the intensity of a light-colored area outside the identifier (or as an area of the identifier) can be preset by adjustment of the power and then the variations in intensity recorded at constant power output while measuring the identifier. The width of the bars and the interstices can be recognized on the basis of the variations in intensity or the intensity sequence.

When use is made of a known intraoral scanning camera for measuring a restoration area and for the subsequent production of design data, an identifier in the form of a bar code showing different intensities of the light-colored and dark-colored areas can be interpreted from a recorded intensity image.

Furthermore, the same intraoral scanning camera can be used to detect relief-coded information and thus recognize it as an identifier.

For this purpose, the workpiece is mounted on a data collection unit 31 illustrated in FIGS. 3, 4 and positioned by a centering bolt 32 cooperating with holder 12 for blank 11 so as to be in exact alignment with a camera guide 33. Scanning camera 34 rests sideways on the top surface of the data collection device 31 and is likewise precisely positioned by supporting and guiding surfaces 35–37. In this position of the workpiece and camera the identifier is recorded and its intensity captured.

It is, of course, possible to place the data collection device 31 in the machining chamber itself, in which case holder 12 will be clamped in workholding device 13 so that the blank to be machined will no longer be removed following recognition of the identifier until machining has been carried out to completion.

Since the exact orientation of the workpiece and the camera discloses where the identifier is mounted on the workpiece, the recording produced by image recognition in this area identifies the bar code.

If the identifier is in the form of a relief, the differences in height will be collected as data, likewise the width of the bars or depressions.

In addition, free-handed recognition of the identifier is conceivable, in which case the area of the identifier will have to be identified by image recognition algorithms.

This is effected by free-handed positioning of the scanning camera on the one hand and of the blank with its identifier on the other hand, and then making an appropriate recording thereof.

The scanning camera operates with a sensor adapted for measurement of height and which is also capable of providing an intensity image, which can be implemented for the recognition of an identifier consisting of different intensities.

The invention claimed is:

1. A measuring device comprising means for measuring models for fabrication of dental fittings involving the production of a three-dimensional data set as template for three-dimensional machining of a workpiece, wherein said measuring means are also adapted for the recognition of an identifier providing information on said workpiece.

2. A measuring device as defined in claim 1, wherein said means for the recognition of an identifier comprise a sensor adapted to recognize an identifier in the form of differences in brightness located on said workpiece.

3. A measuring device as defined in claim 1, wherein said means for the recognition of an identifier comprise a sensor adapted to recognize an identifier in the form of differences in height located on said workpiece.

4. A measuring device as defined in claim 1, wherein said means for the recognition of an identifier comprise a sensor adapted for distance measurement.

5. A measuring device as defined in claim 4, wherein the output of said sensor is governed by the intensity and that the variable controlling said output is dependent on the identifier.

6. A measuring device as defined in claim 1, wherein software for the fabrication of the fitting is present and that said software is designed such that the information gained from the identifier will be taken into consideration for computation of the fitting to be fabricated.

7. A measuring device as defined in claim 1, wherein the identifier can be recognized by the measuring device as a bar code.

8. A measuring device as defined in claim 1, wherein said measuring device forms a component of a machining device for the fabrication of dental fittings from a workpiece, which machining device has a workholding device for said workpiece, which workholding device is also adapted to accommodate a model to be mapped or possesses another workholding device for this purpose, wherein an identifier containing information on said workpiece is provided on said workpiece or said workpiece holder and recognition of said identifier workpiece held in said workholding device is effected by means of said measuring device.

9. A measuring device as defined in claim 8, wherein said measuring device is removably mounted in the machining device for the purpose of measuring a model and for recognizing said identifier.

10. A machining device for the fabrication of dental fittings from a workpiece, comprising a workholding device for said workpiece, wherein an identifier with information on said workpiece is provided on said workpiece or a workpiece holder wherein means for recognizing said identifier on said workpiece held in said workholding device are provided and a single measuring device as defined in claim 1 is provided for the purpose of measuring the model and recognizing said identifier.

11. A machining device as defined in claim 10, wherein said workholding device is also adapted to accommodate a model to be measured.

12. A machining device as defined in claim 11, wherein a holder is provided for releasable accommodation of said measuring device.

13. A machining device as defined in claim 10, wherein software for the fabrication of the fitting is present and that said software is designed such that the information gained from said identifier will be taken into consideration for computation of the fitting to be fabricated.

14. A machining device as defined in claim 10, wherein software for the fabrication of the fitting is present and that said software is designed such that the information gained from said identifier will be taken into consideration for control of said machining device.

15. A machining device as defined in claim 10, wherein software for the fabrication of the fitting is present and that said software is designed such that the information gained from said identifier will be taken into consideration for use for documentation purposes.

16. A measuring device as defined in claim 1, wherein software for the fabrication of the fitting is present and that said software is designed such that the information gained from the identifier will be taken into consideration for control of the machining device.

17. A measuring device as defined in claim 1, wherein software for the fabrication of the fitting is present and that said software is designed such that the information gained from the identifier will be taken into consideration for use for documentation purposes.

* * * * *